(12) United States Patent
Sirkis (10) Patent No.: US 12,171,637 B2
(45) Date of Patent: Dec. 24, 2024

(54) SYSTEM AND METHODS FOR SPEEDING UP THE HEALING OF DENTAL IMPLANTS

(71) Applicant: Rafael Sirkis, Tel Aviv (IL)

(72) Inventor: Rafael Sirkis, Tel Aviv (IL)

(*) Notice: Subject to any disclaimer, the term of this patent is extended or adjusted under 35 U.S.C. 154(b) by 646 days.

(21) Appl. No.: 17/428,007

(22) PCT Filed: Feb. 4, 2020

(86) PCT No.: PCT/IL2020/050131
§ 371 (c)(1),
(2) Date: Aug. 3, 2021

(87) PCT Pub. No.: WO2020/161704
PCT Pub. Date: Aug. 13, 2020

(65) Prior Publication Data
US 2022/0117702 A1 Apr. 21, 2022

Related U.S. Application Data (60) Provisional application No. 62/801,317, filed on Feb. 5, 2019.

(51) Int. Cl.
| | |
|---|---|
| *A61C 8/00* | (2006.01) |
| *A61C 8/02* | (2006.01) |
| *A61N 1/05* | (2006.01) |
| *A61N 1/32* | (2006.01) |

(52) U.S. Cl.
CPC ............ *A61C 8/0007* (2013.01); *A61C 8/008* (2013.01); *A61N 1/0548* (2013.01); *A61N 1/326* (2013.01)

(58) Field of Classification Search
CPC .... A61C 8/0007; A61C 8/008; A61N 1/0548; A61N 1/326

USPC .......................................................... 433/173
See application file for complete search history.

(56) References Cited

U.S. PATENT DOCUMENTS

| | | | | |
|---|---|---|---|---|
| 4,175,565 | A * | 11/1979 | Chiarenza | A61B 17/58 607/51 |
| 5,738,521 | A * | 4/1998 | Dugot | A61C 8/0006 607/51 |
| 7,917,223 | B2 * | 3/2011 | Madjar | A61C 8/0069 607/51 |
| 8,374,697 | B2 * | 2/2013 | Berger | A61B 17/8605 607/51 |
| 9,402,998 | B2 * | 8/2016 | Davidovitch | A61N 1/0548 |
| 9,776,014 | B2 * | 10/2017 | Neuman | A61C 13/0015 |
| 10,039,620 | B2 * | 8/2018 | Brodbeck | A61C 19/06 |
| 11,103,696 | B2 * | 8/2021 | Haralambidis | A61N 1/0548 |
| 11,305,112 | B2 * | 4/2022 | Walser | A61N 1/40 |

(Continued)

FOREIGN PATENT DOCUMENTS

| | | | |
|---|---|---|---|
| CN | 103006343 A | | 4/2013 |
| CN | 103027757 A | * | 4/2013 |

(Continued)

OTHER PUBLICATIONS

International Search Report for Application No. PCT/IL2020/050131, dated May 24, 2020, 3 pages.

(Continued)

*Primary Examiner* — Matthew M Nelson
(74) *Attorney, Agent, or Firm* — Brooks Kushman P.C.

(57) ABSTRACT

Provided herein methods and systems for triggering osteogenesis and promoting osteointegration on dental implants.

12 Claims, 5 Drawing Sheets

(56) References Cited

U.S. PATENT DOCUMENTS

| | | | | |
|---|---|---|---|---|
| 2010/0143871 | A1* | 6/2010 | Berger | A61B 17/8685 |
| | | | | 607/51 |
| 2012/0276501 | A1* | 11/2012 | Terkel | A61C 8/0007 |
| | | | | 433/173 |
| 2014/0023983 | A1* | 1/2014 | Lowe | A61C 7/008 |
| | | | | 433/2 |
| 2014/0141385 | A1* | 5/2014 | Taub | A61B 5/0002 |
| | | | | 433/173 |
| 2015/0343208 | A1* | 12/2015 | Davidovitch | A61C 7/00 |
| | | | | 433/24 |
| 2022/0117702 | A1* | 4/2022 | Sirkis | A61C 8/0007 |

FOREIGN PATENT DOCUMENTS

| | | |
|---|---|---|
| CN | 104207853 A | 12/2014 |
| WO | 2004066851 A2 | 8/2004 |
| WO | 2018160973 A1 | 9/2018 |

OTHER PUBLICATIONS

International Preliminary Report on Patentability for Application No. PCT/IL2020/050131, dated Aug. 10, 2021, 8 pages.
Extended European Search Report for Application No. 20752330.9-1122, dated Feb. 28, 2022, 9 pages.
Chinese Office Action with English translation for Application No. 202080012800.9, dated Dec. 26, 2022, 21 pages.
Israel Office Action and English translation for Application No. 285324, dated Mar. 27, 2024, 12 pages.

\* cited by examiner

[1000] providing to the subject in need a removable apparatus comprising a wearable scaffold, a healing cap and an electronic module

[2000] placing the removable apparatus at the jawbone surrounding in the oral cavity of the subject in need

[3000] conducting the electric current between the jawbone surrounding and the dental implant by mechanically attaching the connector to the mechanical part of the healing cap

SYSTEM AND METHODS FOR SPEEDING UP THE HEALING OF DENTAL IMPLANTS

This application is the U.S. national phase of PCT Application No. PCT/IL2020/050131 filed on Feb. 4, 2020, which claims the benefit of U.S. provisional application Ser. No. 62/801,317 filed Feb. 5, 2019, the disclosures of which are hereby incorporated in their entirety by reference herein.

TECHNICAL FIELD OF THE INVENTION

The invention relates generally to the field of dental implantation, and in particular to methods and systems for triggering osteogenesis and promoting osteointegration on dental implants.

BACKGROUND OF THE INVENTION

Oral rehabilitation treatment, by means of dental implants, is practiced by more and more dentists around the world. There are two major approaches for dental implantation: The classical, conventional approach, which requires long healing time before the completion of the rehabilitation; and the new approach, which is called "All on Four" that promises complete treatment in one day. Unfortunately, the main hardship for both patients and dentists in the conventional approach is the length of healing time following the implantation procedure. To achieve success rates of over 98% a healing time of three to six months is required prior to loading the implant with an artificial tooth or a bridge. As to the "All on Four" approach, the success rate is significantly lower. When the "All on Four" treatment fails, the patient suffers from a great deal of pain and difficulty to eat properly. Moreover, implantation failure presents a serious aesthetic problem. Law suites are frequently filed by patients recovering from unsuccessful "All on Four" implantation.

Electrical Stimulation is known to accelerate and shorten the recovery of bone fractures, and the bone build-up on metallic implants that are used to hold together fractured bones. Such Orthopedic Electrical Stimulation is safely practiced for many years. Numerous studies on animals were conducted and lead to the discovery that electrical stimulation can increase the rate of bone build-up on dental implants as well. As a result, numerous attempts were made to use the orthopedic techniques for teeth implantations in humans. Systems that were developed appeared to be cumbersome and impossible to keep in the oral cavity during the entire healing period. A user-friendly system which will shorten the healing period and improve the recovery, thus remains a long and unmet need.

Currently there is no established method to assess the extent of the recovery following dental implantation, nor is there a product in the market that facilitates the healing process or improves the implant recovery. Given that, a system that will help to improve the success rate of these procedures and to monitor the recovery process is highly desirable and remains a long unmet need.

SUMMARY OF THE INVENTION

Accordingly, it is a principal object of the present invention to overcome the existing challenges in facilitating patient's recovery from dental implantation by inducing osteogenesis in the areas surrounding the implants and promoting osteointegration onto the dental implants thus improving the patient's quality of life.

The invention provides a removable apparatus for stimulation of osteogenesis on at least one dental implant in a subject in need comprising: a) a wearable scaffold designed to fit a jawbone surrounding of the subject and configured to conduct electric current; b) a healing cap, comprising an electrically insulating portion and a current conducting portion, and configured to establish mechanical and electrical interaction with the implant; and, c) an electronic module; wherein the positive terminal of the electronic module is operatively engaged with the conducting area of the wearable scaffold and the negative terminal of the electronic module is operatively engaged with the current conducting portion of the healing cap; and wherein the apparatus is designed to create an electrical current between the jawbone surrounding and the at least one dental implant to thereby stimulate osteogenesis.

The invention further provides a removable dental implant recovery speed-up element comprising a) a wearable scaffold designed to fit a jawbone surrounding of the subject and configured to conduct an electric current; b) a healing cap, comprising an electrically insulating portion and a current conducting portion, and configured to establish mechanical and electrical interaction with at least one dental implant; and, c) an electronic module, wherein the positive terminal of the electronic module is operatively engaged with the conducting area of the wearable scaffold designed to fit a jawbone surrounding of the subject and the negative terminal of the electronic module is operatively engaged with the current conducting portion of the healing cap; and wherein the apparatus is designed to create an electrical current between the jawbone surrounding and the at least one dental implant.

The invention further provides a method of facilitating recovery from dental implantation in a subject in need, comprising: a) providing to the subject in need a removable apparatus comprising a wearable scaffold designed to fit a jawbone surrounding of the subject and configured to conduct electric current; a healing cap, comprising an electrically insulating portion and a current conducting portion, and configured to establish mechanical and electrical interaction with the dental implant; an electronic module comprising a power source and a controller; wherein the positive terminal of the electronic module is operatively engaged with the conducting area in the wearable scaffold designed to fit a jawbone surrounding of the subject and the negative terminal of the electronic module is operatively engaged with the current conducting portion of the healing cap via a connector configured to become mechanically attached to the healing cap and to conduct electrical current when mechanically attached to the current conducting portion of the healing cap; and wherein the apparatus is designed to create an electrical current between the jawbone surrounding and the dental implant; b) placing the apparatus on the jawbone surrounding in the oral cavity of the subject; and, c) conducting the electric current between the jawbone surrounding and the dental implant by mechanically attaching the connector to the current conducting portion of the healing cap.

The invention provides a healing cap for positioning on a dental implant following the procedure of dental implantation, said healing cap comprising: an electrically insulated portion and a current conducting portion, wherein the current conducting portion is configured to penetrate the electrically insulated portion so that one side of the current conducting portion is screwed into a dental implant, and the opposite side of the current conducting portion protrudes from the electrically insulated portion and configured to form a mechanical interaction with a current conducting system to thereby conduct an electric current to the dental implant.

The invention further provides a permanent apparatus for stimulating osteogenesis on a plurality of dental implants, wherein the apparatus is configured to fit the upper and/or lower jaw of a subject in need, said apparatus comprising: a) a full arch prosthesis configured to conduct electric current, wherein said prosthesis is attached to the jaw of the subject by a plurality of screws; and wherein said prosthesis comprises a current conducting unit, wherein said unit comprises a first current conducting element in contact with the gums surrounding the plurality of implants, and a second current conducting element in contact with the plurality of implants via the plurality of screws; b) a plurality of abutments configured allow passage of the screws and to become engaged in mechanical and electrical interaction with the plurality of implants, wherein said abutments are made of electrically insulating material; and, c) an electronic module, wherein the positive terminal of the electronic module is operatively engaged with the first conducting element of full arch prosthesis and the negative terminal of the electronic module is operatively engaged with the second conducting element of the full arch prosthesis.

The invention yet further provides a method of stimulating osteogenesis on a plurality of dental implants in a subject in need, comprising a) providing the subject in need with the permanent apparatus of the invention; b) attaching the apparatus to the jaw in the oral cavity of the subject; and, c) conducting sufficient electrical current between the gums surrounding the plurality of implants to thereby effectively stimulate osteogenesis.

The invention yet further provides a method of promoting osteointegration on a plurality of dental implants in a subject in need, comprising a) providing the subject in need with the permanent apparatus of the invention; b) attaching the apparatus to the jaw in the oral cavity of the subject; and, c) conducting sufficient electrical current between the gums surrounding the plurality of implants to thereby effectively stimulate osteogenesis.

BRIEF DESCRIPTION OF THE DRAWINGS

FIG. 1A,B: Illustrates an exemplary embodiment of two removeable scaffolds: A. illustrates the apparatus suitable for the lower jaw of the patient. B. Illustrates the apparatus suitable for the upper jaw of the patient;

DETAILED DESCRIPTION OF THE INVENTION

Before explaining at least one embodiment of the invention in detail, it is to be understood that the invention is not limited in its application to the details of construction and the arrangement of the components set forth in the following description or illustrated in the drawings. The invention is applicable to other embodiments being practiced or carried out in various ways. Also, it is to be understood that the phraseology and terminology employed herein is for the purpose of description and should not be regarded as limiting.

The invention provides treatment option for patients undergoing recovery from dental implantation. In particular, the invention provides removeable and permanent apparatuses which facilitate osteogenesis and promote osteointegration on the dental implant/s.

Figure 1:
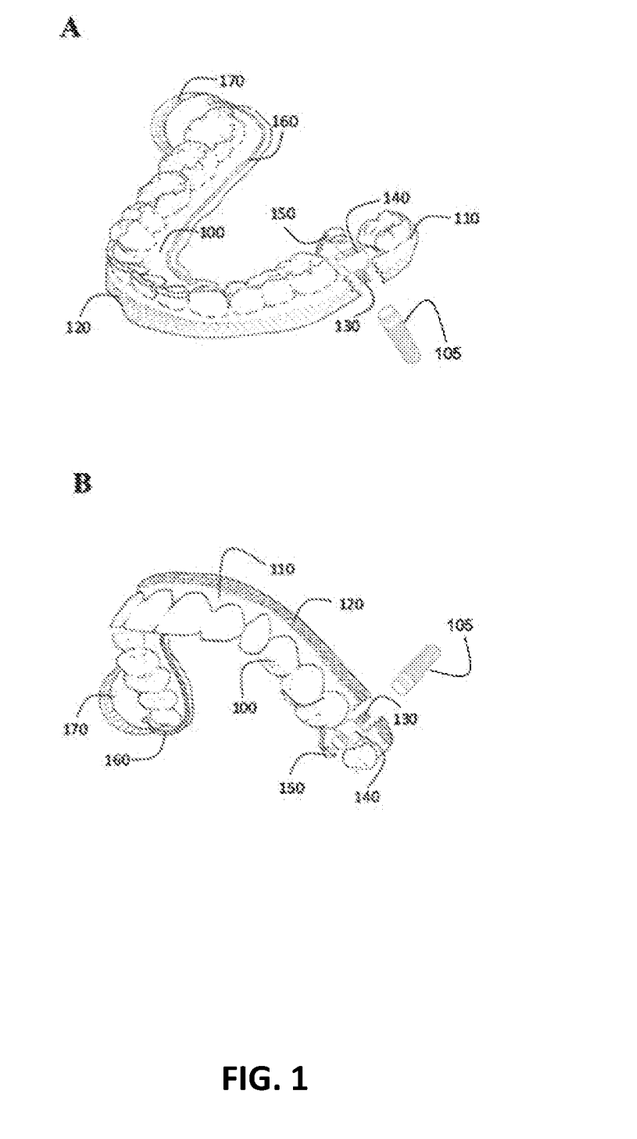

According to some embodiments, the invention provides removable apparatus for stimulation of osteogenesis on at least one dental implant. Reference is now made to FIG. 1(A,B) illustrating an exemplary embodiment of a removable apparatus for stimulation of osteogenesis and promoting osteointegration on dental implant suitable for lower (FIG. 1A) and upper (FIG. 1B) jaw of a subject in need. The apparatus comprises: a) a wearable scaffold designed to fit a jawbone surrounding 110 and configured to conduct electric current; b) a healing cap 140, comprising an electrically insulating portion and a current conducting portion, and configured to establish mechanical and electrical interaction with the implant 105 via the mechanical part 130; and, c) an electronic module 170; wherein the positive terminal of the electronic module 170 is operatively engaged with the conducting area 120 of the wearable scaffold 110 and the negative terminal of the electronic module 170 is operatively engaged with the healing cap 140; and wherein the apparatus is designed to create an electrical current between the jawbone surrounding 100 and the dental implant 105 via the mechanical part 130. In the context of the invention, the term "subject in need" refers, without limitation, to a human subject who underwent dental implantation and has at least one dental implant in the oral cavity. In one embodiment, the apparatus is configured to promote osteointegration on more than one dental implant simultaneously. For the sake of clarity, the term "jawbone surrounding" includes gums or tissue that surrounds the necks of teeth and covers the alveolar parts of the jaws broadly, in other words, the alveolar portion of a jaw with its enveloping soft tissues. As used herein, the term "wearable scaffold designed to fit a jawbone surrounding" refers, without limitation, to dental splints formed to exactly be mounted over the teeth and gums of the patient. An opening is cut in the splint at the location of the dental implant(s), to allow the healing cap(s) mounted on the dental implant(s) to go through the splint and be accessible to electrical connection. The locations of such openings can be over any other location in which a dental implant is implanted.

The wearable scaffold of the invention 110 is designed to conduct electric current. In one embodiment, the wearable scaffold 110 is designed to conduct electric current on its side touching the gums. In one embodiment, the wearable scaffold 110 comprises electric current conducting area 120. The conducting area 120 of the wearable scaffold 110 comprises media capable to conduct electric current. The media can be, without limitation, in the form of a coating of the wearable scaffold 110, an add-on element attached to the wearable scaffold 110, in the form of electric current conducting material embedded in the wearable scaffold 110, or in any other form which confer electrical conductivity to the wearable scaffold 110 of the invention. According to the embodiments of the invention, the conducting area 120 of the wearable scaffold 110 is operatively engaged with the positive terminal of the electronic module 170.

Figure 3:
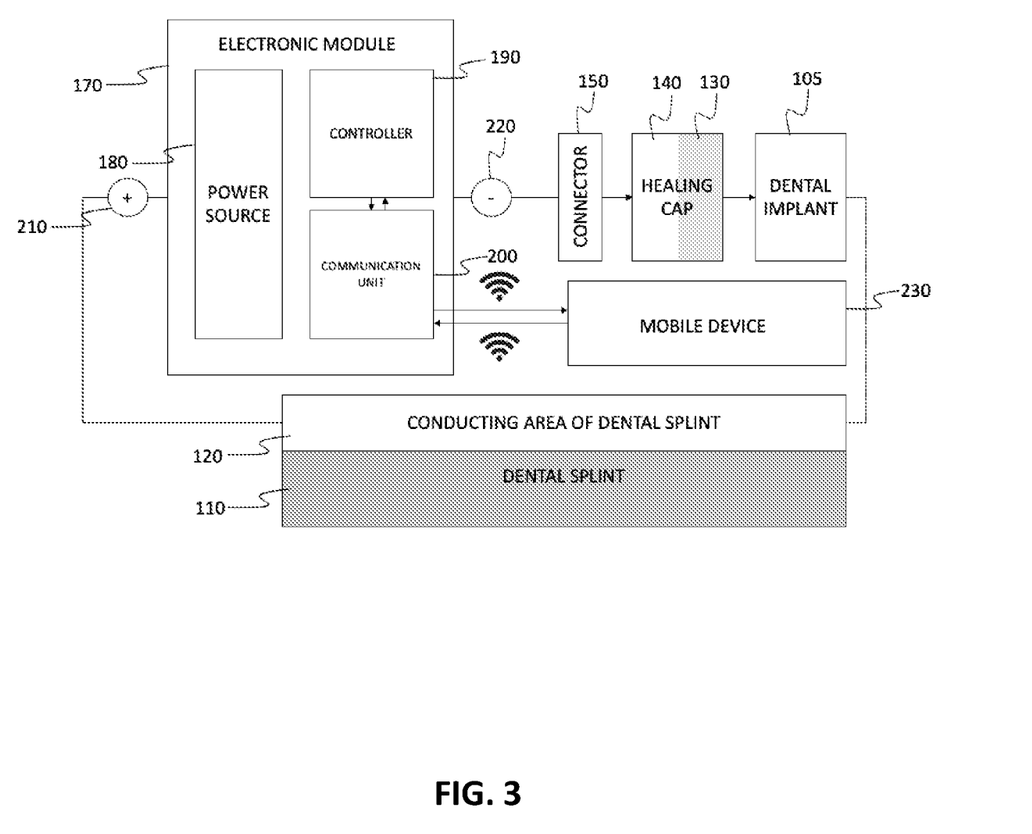
FIG. 3: A functional block diagram representing the system for facilitating osteogenesis and promoting osteointegration following dental implantation.

Reference is now made to FIG. 3, which is a functional block diagram of an exemplary embodiment of the system for facilitating osteogenesis and promoting osteointegration. In one embodiment, the electronic module 170 of the invention comprises a power source 180 and a controller 190. In one embodiment, the electronic module 170 further comprises a communication element 200. As used herein, the term "power source" refers, but not limited to primary or chargeable batteries, having the capacity to provide energy to operate the electronic parts within the electronic module 170, as well as provide the required healing current to the implant. In one embodiment, the wearable scaffold is a vacuum formed custom dental splint. The controller of the invention is configured to perform, without limitation, at least one of the following functions: a) measure the ohmic resistance of the bone-implant interface to the electrical current; b) record the measured data; c) transmit the data to the wireless communication element and, d) control the electrical current flow between the jawbone surrounding and the dental implant. In one embodiment, the wireless communication element is configured to fulfill, without limitation, at least one of the following functions: a) transmit the data recorded by the controller to a mobile device 230; b) to receive instructions from the mobile device 230, and c) to transmit said instructions to the controller 190. In one embodiment, the communication element 200 is a wireless communication element. In another embodiment, wireless communication element 200 is configured to communicate to the user the status of the power source 180. In yet further embodiment, the controller is configured to control the magnitude of the electric current. In yet further embodiment, the controller is a digital chip. In one embodiment, the electric current flowing between the jawbone surrounding and the implant has the magnitude in the range of 2 to 20 micro-Amperes. According to one embodiment, the recorded data are transferred by the communication element 200 to the mobile device 230 wirelessly. In one embodiment, recorded data are transferred using Bluetooth.

Figure 2:
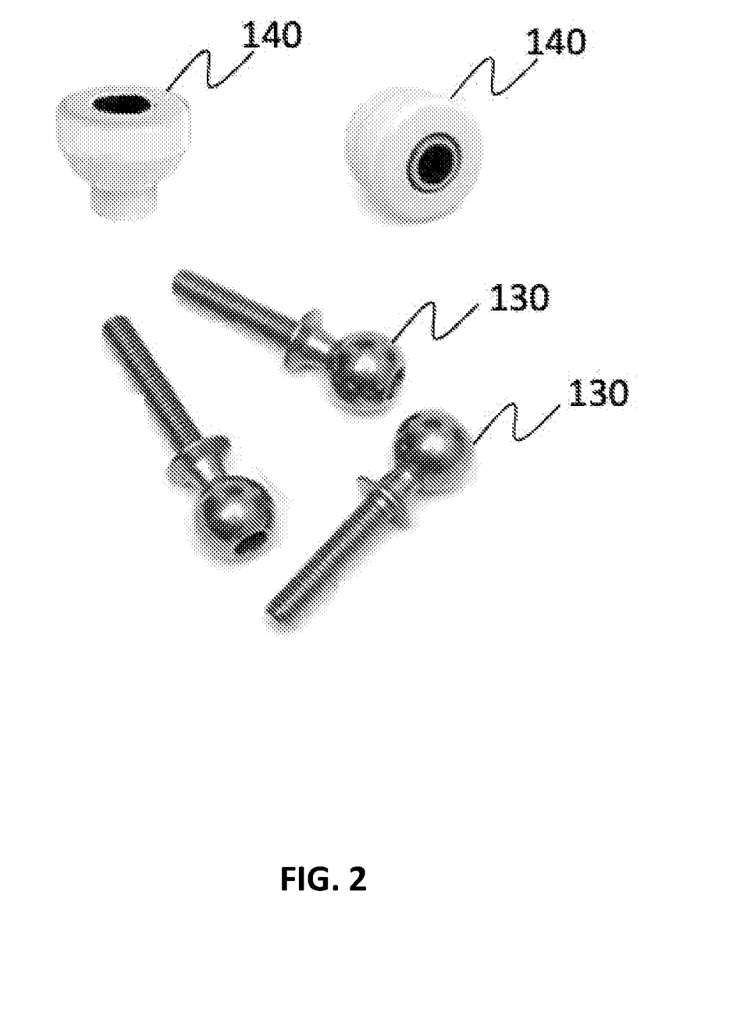
FIG. 2: Illustrates an exemplary embodiment of a novel healing cap for an individual dental implant.

Reference is now made to FIG. 2 illustrating an exemplary embodiment of the mechanical part 130 and the healing cap 140 of the invention. In one embodiment the mechanical part 130 is configured to form a ball shaped contact to mate with a Snap-On connector (FIG. 1) which terminates the wire 160 coming from the electronic module 170. Inside the ball there is a standard hexagonal opening enabling the use of standard tightening tool to turn the mechanical part 130. The mechanical part 130 has a long-threaded part that goes through the healing cap 140 and is screwed into the dental implant (FIG. 1). As used herein, the term "electrical interaction" refers, but not limited to an electromagnetic interaction between charged particles arising from their electric and magnetic fields. According to some embodiments, the apparatus further comprises a Snap-On connector 150 (FIG. 1) designed to become mechanically attached to the mechanical part 130. In one embodiment, the connector is operatively engaged with the negative portal of the electronic module (FIG. 1). In the context of the invention, as used herein the term "healing cap" refers, but not limited to an article of manufacture designed to protect the internal aspects of the implant from debris accumulations. The healing cap serves as the initial transmucosal connection between the external environment and the inner parts of the human body and forms a bacteriological barrier with a tight connection between the epithelium and implant component, thus helping to prevent infection, crestal bone loss and soft tissue recession. According to some embodiments, the healing cap of the invention is made of electrically insulating material and configured to establish mechanical and electrical interaction with the implant, via the mechanical part 130. According to some embodiments, the healing cap is made of zirconium. Additional, non-limiting examples of electrically insulating materials suitable for healing caps are plastic materials such as Peek, or any other insulating materials approved for dental use.

According to some embodiments, the invention provides a removable dental implant recovery speed-up element comprising a) a wearable scaffold designed to fit a jaw bone surrounding of the subject and configured to conduct an electric current; b) a healing cap, comprising an electrically insulating portion and a current conducting portion, and configured to establish mechanical and electrical interaction with at least one dental implant; and, c) an electronic module, wherein the positive terminal of the electronic module is operatively engaged with the conducting area of the a wearable scaffold designed to fit a jaw bone surrounding of the subject and the negative terminal of the electronic module is operatively engaged with the current conducting portion of the healing cap; and wherein the apparatus is designed to create an electrical current between the jaw bone surrounding and the at least one dental implant. According to some embodiments, the controller is configured to fulfill at least one of the functions selected from: a) measuring the ohmic resistance of the bone-implant interface to the electrical current; b) recording the measured data; c) transmitting the data to a mobile device in communication with the controller; and, d) controlling the electrical current flow between the jaw bone surrounding and the dental implant. As used herein, the term "recovery" is meant to be understood as a process of healing, or gaining back the capability, function or quality of life, whether fully or partially, which one had prior to the dental implantation.

Figure 4:
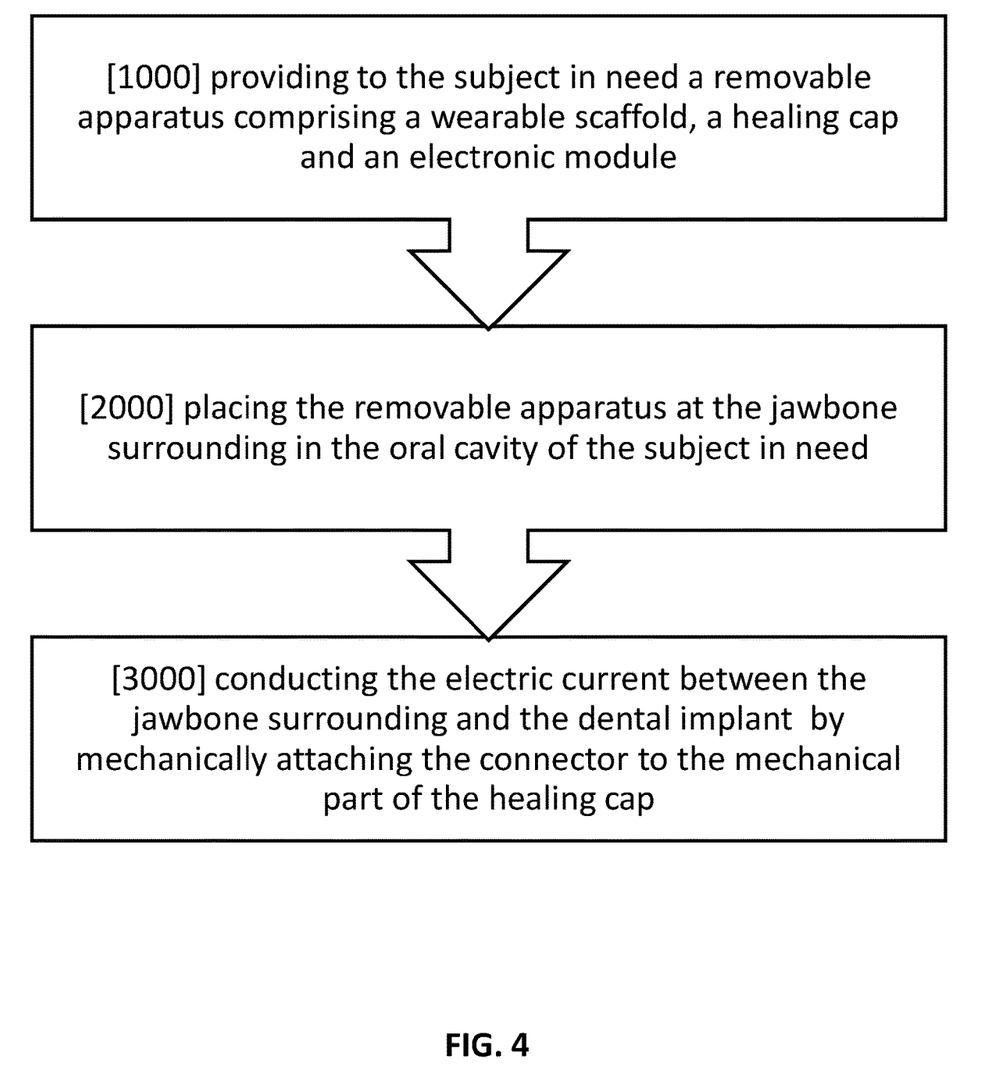
FIG. 4: A flowchart representing an exemplary embodiment of a method of facilitating recovery from dental implantation.

Reference is now made to FIG. 1, FIG. 3 and FIG. 4. FIG. 4 provides a flowchart of an exemplary embodiment of a method of facilitating recovery from dental implantation, in a subject in need comprising: [1000] providing to the subject in need a removable apparatus comprising a wearable scaffold designed to fit a jawbone surrounding 110 and configured to conduct electric current; a healing cap 140 made of electrically insulating material and configured to establish mechanical and electrical interaction with the implant 105; an electronic module 170 comprising a power source 180; a controller 190; and a wireless communicating unit 200; wherein the positive terminal 210 of the electronic module is operatively engaged with the conducting area 120 in the wearable scaffold 110 and the negative terminal 220 of the electronic module is operatively engaged with the healing cap 140 via a connector configured to become mechanically attached to the healing cap 140 and to conduct electrical current when mechanically attached to the healing cap 140; and wherein the apparatus is designed to create an electrical current between the jawbone surrounding and the dental implant 105; [2000] placing the removable apparatus at the jawbone surrounding in the oral cavity of the subject in need; and [3000] conducting the electric current between the jawbone surrounding and the dental implant 105 by mechanically attaching the connector to the mechanical part 130 of the healing cap 140. In one embodiment, the apparatus is placed at the surrounding of the upper jawbone. In another embodiment, the apparatus is placed at the surrounding of the lower jawbone. In yet further embodiment, the apparatus is placed at the surrounding of the upper and the lower jawbone. In one embodiment, the electric current between the jawbone surrounding and the dental implant has the magnitude of 2 to 20 micro-Ampere. In one embodiment, the method further comprises measuring ohmic resistance of the bone-implant interface to the electrical current by a controller 190 of the electronic module 170. In another embodiment, the method comprises recording subject's data by the controller. In yet further embodiment, the recorded data is transferred to a mobile device 230. As used herein, the term "mobile device" refers, but not limited to any portable computing electronic device small enough to be carried around. In the method of the invention electric current flow between the jawbone surrounding and the dental implant 105 can be interrupted by the controller 190. In one embodiment, the apparatus is placed at the surrounding of the jawbone repeatedly for a predetermined time interval over a predetermined period of time. In one embodiment, the apparatus is placed at the surrounding of the jawbone during the sleep time. In yet another embodiment, the apparatus is placed at the surrounding of the jawbone repeatedly until the end of the healing period.

Figure 5:
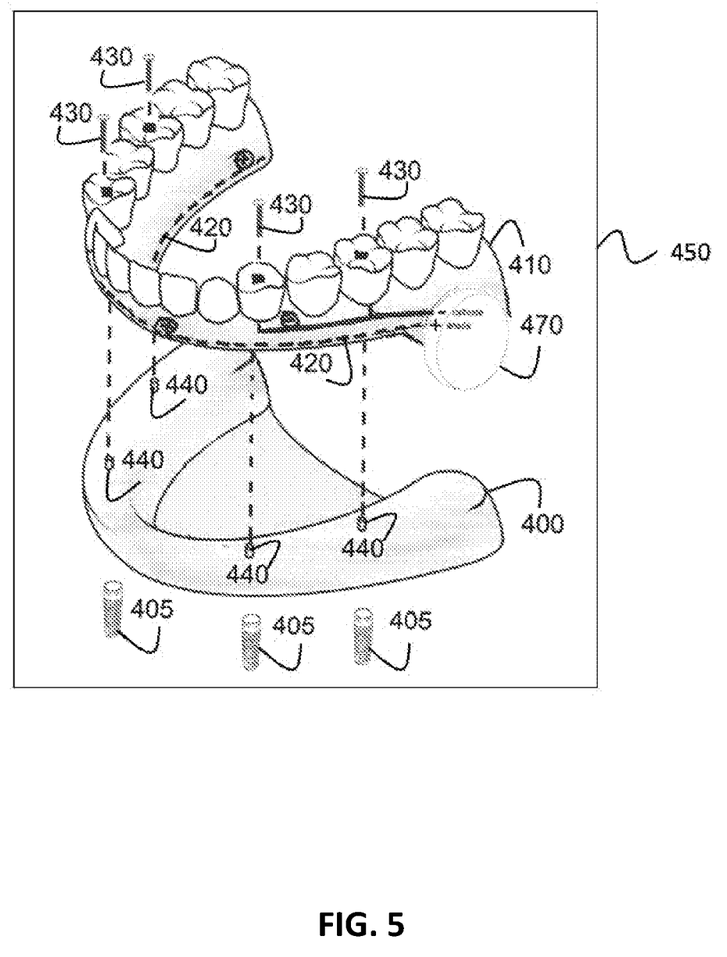
FIG. 5: Illustrates an exemplary embodiment of a permanent apparatus facilitating osteogenesis and promoting osteointegration.

According to some embodiments, the invention provides a permanent apparatus for stimulating osteogenesis on a plurality of dental implants, wherein the apparatus is configured to fit the upper and/or lower jaw of a subject in need, said apparatus comprising: a) a full arch prosthesis configured to conduct electric current, wherein said prosthesis is attached to the implants in jaw of the subject by a plurality of screws; and wherein said prosthesis comprises a current conducting unit, wherein said unit comprises a first current conducting element in contact with the gums surrounding the plurality of implants, and a second current conducting element in contact with the plurality of implants via the plurality of screws; b) a plurality of abutments configured allow passage of the screws and to become engaged in mechanical and electrical interaction with the plurality of implants, wherein said abutments are made of electrically insulating material; and, c) an electronic module, wherein the positive terminal of the electronic module is operatively engaged with the first conducting element of full arch prosthesis and the negative terminal of the electronic module is operatively engaged with the second conducting element of the full arch prosthesis. Reference is now made to FIG. 5 Illustrating an exemplary embodiment of a permanent prosthesis suitable for the lower jaw of the subject in need. The permanent apparatus comprises: a) a full arch prosthesis 410 configured to conduct electric current, wherein said prosthesis is attached to the lower jaw of the subject 400 by a plurality of screws 430; and wherein said prosthesis comprises a current conducting unit, wherein said unit comprises a first current conducting element in contact with the gums 410 surrounding the plurality of implants 405, and a second current conducting element in contact with the plurality of implants 405 via the plurality of screws 430; b) a plurality of abutments 440 configured allow passage of the screws 430 and to become engaged in mechanical and electrical interaction with the plurality of implants 405, wherein said abutments 440 are made of electrically insulating material; and, c) an electronic module 470; wherein the positive terminal of the electronic module 470 is operatively engaged with two bare wires 420 embedded into the sides of the permanent prosthesis 410, touching the gums 400 and the negative terminal of the electronic module 470 is operatively engaged with insulated wires going to the plurality of screws 430 of the permanent prosthesis. In one embodiment, the apparatus is designed to create an electrical current between the bare embedded wires touching the gums of the jawbone surrounding 400 and the dental implants 405, via the retaining screws 430 and the abutments 440. According to some embodiments, the electrical connection is made via a connector to which the wires embedded in the prosthesis are connected. The negative terminal connects to the embedded wires going to the screws of the prosthesis. The positive terminal connects to the embedded wires touching the gums. In this way an electrical circuit, enabling the flow of electrical current between the jawbone surrounding and the dental implants is created.

According to some embodiments, the electronic module is a detachable electronic module. As used herein, the term "detachable" is meant to be understood as able to be removed or separated, either temporarily or permanently. According to some embodiments, the current conducting unit is a current conducting insulated wire. The current conducting unit of the invention can be, without limitation, in the form of stainless-steel wires embedded in the prosthesis or in any other form that confers electric current conductivity to the full arch prosthesis.

According to some embodiments, the permanent apparatus further comprises a housing designed to enclose the electronic module.

In one embodiment, the electronic module comprises a power source and a controller. In another embodiment, the electronic module further comprises a wireless communication element.

According to some embodiments, the controller is configured to fulfill at least one of the functions selected from: a) measure the ohmic resistance of the bone-implant interface to the electrical current; b) record the measured data; c) transmit the data to the wireless communication element; d) control the electrical current flow between the jaw bone surrounding and the dental implant. According to some embodiments, the wireless communication element is configured to fulfill at least one of the functions selected from: a) receive the data recorded by the controller; b) transmit the recorded data to a mobile device; c) receive instructions from the mobile device to control the electric current, d) transmit the instructions to control the electric current to the controller.

According to some embodiments, the invention provides a method of stimulating osteogenesis on a plurality of dental implants in a subject in need, comprising a) providing the subject in need with the permanent apparatus of the invention; b) attaching the apparatus to the jaw in the oral cavity of the subject; and, c) conducting sufficient electrical current between the gums surrounding the plurality of implants to thereby effectively stimulate osteogenesis.

According to some embodiments, the invention provides a method of promoting osteointegration on a plurality of dental implants in a subject in need, comprising a) providing the subject in need with the permanent apparatus of the invention; b) attaching the apparatus to the jaw in the oral cavity of the subject; and, c) conducting sufficient electrical current between the gums surrounding the plurality of implants to thereby effectively stimulate osteogenesis.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof. As used herein the terms "comprises", "comprising", "includes", "including", "having" and their conjugates mean "including but not limited to". The term "consisting of" means "including and limited to".

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "operatively coupled" to, "operatively linked" to, "operatively engaged" with, "connected" to, "coupled" with, "contacting," etc., another element, it can be directly on, attached to, connected to, operatively coupled to, operatively engaged with, coupled with and/or contacting the other element or intervening elements can also be present. In contrast, when an element is referred to as being "directly contacting" another element, there are no intervening elements present.

Whenever the term "about" is used, it is meant to refer to a measurable value such as an amount, a temporal duration, and the like, and is meant to encompass variations of ±20%, ±10%, +5%, ±1%, or ±0.1% from the specified value, as such variations are appropriate to perform the disclosed methods. Whenever the term "about" is used, it is meant to refer to a measurable value such as an amount, a temporal duration, and the like, and is meant to encompass variations of ±20%, ±10%, ±5%, ±1%, or +0.1% from the specified value, as such variations are appropriate to perform the disclosed methods.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section.

Whenever terms "plurality" and "a plurality" are used it is meant to include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention.

Certain features described in the context of various embodiments are not to be considered essential features of those embodiments, unless the embodiment is inoperative without those elements.

Throughout this application, various embodiments of this invention may be presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In case of conflict, the patent specification, including definitions, will prevail. In addition, the materials, methods, and examples are illustrative only and not intended to be limiting. Throughout this application various publications, published patent applications and published patents are referenced.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A removable apparatus for stimulation of osteogenesis on at least one dental implant in a subject in need comprising: a) a wearable scaffold designed to fit a jawbone surrounding of the subject and configured to conduct electric current; b) a healing cap, comprising an electrically insulating portion and a current conducting portion, and configured to establish mechanical and electrical interaction with the implant; and, c) an electronic module; wherein the positive terminal of the electronic module is operatively engaged with the conducting area of the wearable scaffold and the negative terminal of the electronic module is operatively engaged with the current conducting portion of the healing cap; and wherein the apparatus is designed to create an electrical current between the jawbone surrounding and the at least one dental implant to thereby stimulate osteogenesis.

2. The apparatus of claim 1, further comprising a snap-on connector designed to become mechanically attached to the current conducting portion of the healing cap; wherein the connector is operatively engaged with the negative terminal of the electronic module and configured to conduct electrical current when mechanically attached to the current conducting portion of healing cap.

3. The apparatus of claim 2, wherein the snap-on connector is operatively engaged with the negative terminal of the electronic module via an insulated electrical wire.

4. The apparatus of claim 1, further comprising a housing designed to enclose the electronic module.

5. The apparatus of claim 1, wherein the electronic module comprises a power source a controller, and, optionally, a wireless communication element.

6. The apparatus of claim 5, wherein the controller is configured to fulfill at least one of the functions selected from: a) measuring the ohmic resistance of the bone-implant interface to the electrical current; b) recording subject's data; c) transmitting subject's data to the wireless communication element; and, d) controlling the electrical current between the jawbone surrounding and the at least one dental implant.

7. The apparatus of claim 6, wherein the wireless communication element is configured to fulfill at least one of the functions selected from: a) receiving subject's data by the controller; b) transmitting subject's data to a mobile device; c) receiving instructions from the mobile device to control the electrical current; and, d) transmitting instructions to control the electrical current to the controller.

8. The apparatus of claim 7, wherein the subject's data are transmitted from the controller to the wireless communication element and from the wireless communication element to the mobile device wirelessly; and, optionally, wherein the data are transmitted by means of Bluetooth technology.

9. A removable dental implant recovery speed-up element comprising a) a wearable scaffold designed to fit a jawbone surrounding of the subject and configured to conduct an electric current; b) a healing cap, comprising an electrically insulating portion and a current conducting portion, and configured to establish mechanical and electrical interaction with at least one dental implant; and, c) an electronic module, wherein the positive terminal of the electronic module is operatively engaged with the conducting area of the wearable scaffold designed to fit a jawbone surrounding of the subject and the negative terminal of the electronic module is operatively engaged with the current conducting portion of the healing cap; and wherein the apparatus is designed to create an electrical current between the jawbone surrounding and the at least one dental implant.

10. The dental implant recovery speed-up element of claim 9, further comprising a controller, wherein the controller is configured to fulfill at least one of the functions selected from: a) measuring the ohmic resistance of the bone-implant interface to the electrical current; b) recording subject's data; c) transmitting subject's data to a mobile device in communication with the controller; and, d) controlling the electrical current between the jawbone surrounding and the dental implant.

11. A method of facilitating recovery from dental implantation in a subject in need, comprising: a) providing to the subject in need a removable apparatus of claim 2; b) placing the apparatus on the jawbone surrounding in the oral cavity of the subject; and, c) conducting the electric current between the jawbone surrounding and the dental implant by mechanically attaching the snap-on connector to the current conducting portion of the healing cap.

12. The method of claim 11, wherein the removable apparatus further comprises a controller, and wherein the controller is configured to fulfill at least one of the functions selected from: a) measure the ohmic resistance of the bone-implant interface to the electrical current; b) record subject's data; and, c) control the electrical current between the jawbone surrounding and the dental implant.

* * * * *